United States Patent
Ripart

(10) Patent No.: US 7,483,740 B2
(45) Date of Patent: Jan. 27, 2009

(54) ACTIVE IMPLANTABLE MEDICAL DEVICE WHICH INCLUDES A MODE OF RESYNCHRONIZATION OF THE VENTRICULAR CONTRACTIONS FOR THE TREATMENT OF THE CARDIAC INSUFFICIENCY

(75) Inventor: Alain Ripart, Gif sur Yvette (FR)

(73) Assignee: Ela Medical S.A.S., Montrouge (FR)

( * ) Notice: Subject to any disclaimer, the term of this patent is extended or adjusted under 35 U.S.C. 154(b) by 128 days.

(21) Appl. No.: 11/197,124

(22) Filed: Aug. 3, 2005

(65) Prior Publication Data
US 2006/0079940 A1    Apr. 13, 2006

(30) Foreign Application Priority Data
Aug. 4, 2004    (FR) .................... 04 08609

(51) Int. Cl.
*A61N 1/362*    (2006.01)
(52) U.S. Cl. ......................................... 607/9
(58) Field of Classification Search ............ 607/9
See application file for complete search history.

(56) References Cited

U.S. PATENT DOCUMENTS

| 4,945,909 A | | 8/1990 | Fearnot et al. | |
| 5,334,222 A | | 8/1994 | Salo et al. | |
| 5,626,623 A | * | 5/1997 | Kieval et al. | 607/23 |
| 5,873,895 A | | 2/1999 | Sholder et al. | |
| 6,456,880 B1 | * | 9/2002 | Park et al. | 607/25 |
| 6,473,645 B1 | * | 10/2002 | Levine | 607/9 |
| 6,522,923 B1 | * | 2/2003 | Turcott | 607/27 |
| 6,666,826 B2 | * | 12/2003 | Salo et al. | 600/485 |
| 2002/0151935 A1 | * | 10/2002 | Levine | 607/9 |
| 2002/0161410 A1 | * | 10/2002 | Kramer et al. | 607/9 |
| 2003/0078625 A1 | * | 4/2003 | Casavant | 607/9 |

FOREIGN PATENT DOCUMENTS

| EP | 0 600 631 A2 | 6/1994 |
| EP | 1 108 446 A1 | 6/2001 |

* cited by examiner

*Primary Examiner*—Carl H. Layno
*Assistant Examiner*—Jon-Eric C. Morales
(74) *Attorney, Agent, or Firm*—Orrick Herrington & Sutcliffe, LLP

(57) ABSTRACT

An active implantable medical device including a generator connected to a right ventricular electrode and a left ventricular electrode. The generator includes two output terminals connected to the ventricular electrodes, to deliver joint stimulation impulses with an adjustable inter-ventricular delay. The generator is a generator of the double chamber pacemaker type including an atrial terminal, a ventricular terminal, and circuits for jointly delivering at the atrial and ventricular terminals stimulation impulses with an adjustable atrio-ventricular delay. One of the outputs is the atrial terminal and the other is the ventricular terminal, the atrio-ventricular delay being adjusted with the value of the inter-ventricular delay.

12 Claims, 1 Drawing Sheet

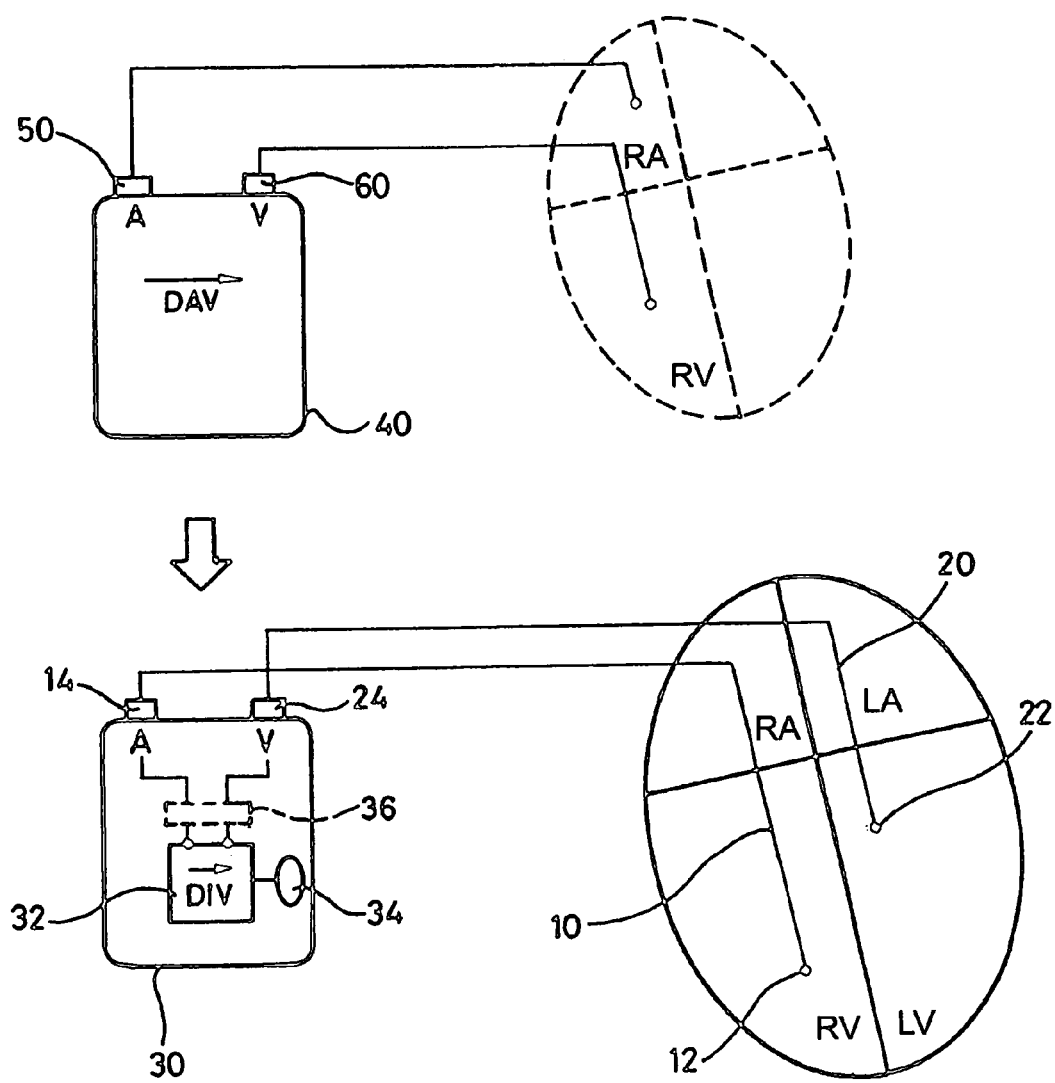
FIG_1

ACTIVE IMPLANTABLE MEDICAL DEVICE WHICH INCLUDES A MODE OF RESYNCHRONIZATION OF THE VENTRICULAR CONTRACTIONS FOR THE TREATMENT OF THE CARDIAC INSUFFICIENCY

FIELD OF THE INVENTION

The present invention relates to "active implantable medical devices" as defined by the Jun. 20, 1990 directive 90/385/CEE of the Council of European Communities, and more precisely to devices known as cardiac pacemakers, defibrillators, and/or cardiovertors that are able to deliver to the heart pulses of low energy for treatment of cardiac rhythm disorders. The invention more particularly relates to devices of this type that are capable of ensuring stimulation of both the left and right ventricles of the heart in order to resynchronize the two ventricles.

BACKGROUND OF THE INVENTION

These devices are composed of a case or "generator," including a power supply and the electronics of the device, and probes connected to the generator that are equipped with sensing/stimulation electrodes in contact with atrial and/or ventricular sites of the myocardium of a patient's heart.

As an alternative to or complementary with cardiac rhythm disorders, it was proposed to treat with bi-ventricular stimulation some myocardic contraction disorders observed among patients in cardiac insufficiency. These disorders can be spontaneous or induced by a traditional stimulation. The publication of J. C. Daubert et al., Stimucoeur, 25, n °3, pp. 170-176, gives a description of this. This bi-ventricular stimulation therapy often resulted in spectacular results for patients in class III cardiac insufficiency whose conditions were not improved by traditional treatments.

The first known devices of this type operated in synchronous stimulation, i.e., the two ventricular sites received a depolarization impulse at the same time with no inter-ventricular delay. More recent devices, such as those described, for example, in EP-A-1 108 446 and its counterpart U.S. Pat. No. 6,556,866 (which U.S. patent is incorporated herein by reference), both assigned herewith to ELA Médical, Montrouge, France, instead operate in a synchronous and controlled mode, by applying a variable inter-ventricular delay (DIV) between two stimulations, adjusted so as to resynchronize contraction of the ventricles with fine optimization of the hemodynamic state of the patient. The devices used currently for this purpose are "multisite" prostheses in which electrodes are placed in a plurality of distinct sites comprising the right and left ventricular sites and at least one atrial site. The devices can also be of the "triple chamber" (double ventricular stimulation and right atrial detection/stimulation) or "quadruple chamber" (double ventricular stimulation and double atrial detection/stimulation) types. EP-A-0 925 806 and its counterpart, U.S. Pat. No. 6,253,106 (which U.S. patent is incorporated herein by reference), both assigned herewith to ELA Médical, describe such multisite devices, comprising in particular means for selecting a stimulation configuration best suited for the patient.

The starting point of the present invention is the observation that the majority of patients receiving such implanted multisite devices typically present a normal atrio-ventricular conduction (where each atrial event is followed by an associated spontaneous ventricular depolarization) and therefore do not have a standard indication for implantation of a pacemaker. The triple or quadruple chamber multisite devices used for this purpose, when suitably parameterized to ensure a bi-ventricular stimulation, operate satisfactorily on a clinical level. But such devices are relatively sophisticated and therefore can be expensive and difficult to program, while at the same time a number of functions they are capable of performing go unused.

OBJECTS AND SUMMARY OF THE INVENTION

One of the goals of the present invention is to propose an active implantable medical device especially adapted to joint stimulation of the ventricles in order to resynchronize the ventricles, which is a simpler configuration than the prior art multisite triple or quadruple chamber devices used for this purpose.

Another goal of the invention is reduction of the unit cost of the devices intended for bi-ventricular stimulation by using hardware identical to that already existing in known pacemakers, and consequently allowing implementation of the invention without significant additional cost, through an adaptation of the control software.

The present invention is directed to using a conventional double chamber generator of the DDD pacemaker type, i.e., originally intended for an atrio-ventricular stimulation, and adapting this device to make it capable of a bi-ventricular stimulation. This adaptation can be carried out by a simple modification of the control software of the generator. Thus, because the hardware part of the device is identical to what already exists for a DDD pacemaker, bi-ventricular stimulation can be implemented without significant additional cost.

This DDD generator, adapted to allow a bi-ventricular stimulation, will be connected to left and right ventricular stimulation probes of a known type, resulting in a device that can ensure joint and permanent left and right ventricular stimulation in order to resynchronize the contraction and, consequently, to improve the general hemodynamic state of the patient.

More precisely, the invention relates to an implantable medical device including a mode of resynchronizing ventricular contractions for treatment of cardiac insufficiency. A device of this type, disclosed, for example, by the above-mentioned EP-A-1 108 446 and U.S. Pat. No. 6,556,866 (which U.S. patent is incorporated herein by reference), includes a generator combined with a first probe provided with a left ventricular electrode, and with a second probe, equipped with a right ventricular electrode. The generator includes a first output, connected to the left ventricular electrode, and a second output, connected to the right ventricular electrode. It also includes means of right and left ventricular stimulation, able to jointly deliver stimulation impulses to the left and right ventricular electrodes, as well as means for establishing an adjustable inter-ventricular delay between application of the impulses delivered to the right and left ventricular electrodes, respectively, during the same cardiac cycle.

In one preferred embodiment of the invention, the generator is of the double chamber pacemaker type, i.e., it includes an atrial terminal and a ventricular terminal; means for atrial and ventricular stimulation, able to jointly deliver to the atrial and ventricular terminals respective stimulation impulses; and means for establishing an adjustable atrio-ventricular delay between the moments of application of the impulses respectively delivered to the atrial terminal and the ventricular terminal. One of the aforesaid first and second outputs of the device is the atrial terminal of the double chamber generator, and the other output terminal is the ventricular terminal, the atrio-ventricular delay being adjusted with the value of the aforesaid inter-ventricular delay.

The means for establishing an adjustable atrio-ventricular delay can either be means able to give a positive, null, or negative value to this atrio-ventricular time interval, or means able to give a positive or null value to this atrio-ventricular time, the device comprising switching means for permuting the atrial and ventricular terminals such that, given the same cardiac cycle, the terminals can be switched to a first condition where the ventricular terminal can deliver an impulse before or simultaneous with the ventricular terminal, and a second condition where the atrial terminal delivers an impulse before or simultaneous with the ventricular terminal.

Optionally, the device can include a sensor of a hemodynamic parameter, combined with suitable control means, according to a signal delivered by the sensor, for adjusting the adjustable atrio-ventricular delay in a direction of an improvement of the sensed hemodynamic parameter.

The device also can include means for analyzing a parameter representative of the degree of desynchronization between ventricles over a cardiac cycle, combined with the control means, according to a signal delivered by these means of analysis, for varying the adjustable atrio-ventricular delay in a direction of reduction in this degree of desynchronization.

BRIEF DESCRIPTION OF THE DRAWING

Further benefits, features, and characteristics of the present invention will become apparent to a person of ordinary skill in the art in view of the following detailed description of the invention, made with reference to the annexed drawing, where FIG. 1 schematically illustrates a device according to the invention, and the manner of carrying it out starting from a double chamber DDD generator.

DETAILED DESCRIPTION OF THE INVENTION

With regard to its software aspects, the present invention can be implemented by suitable programming of the control software of known pacemakers. The invention can in particular be applied to the implantable devices marketed by ELA Médical, Montrouge, France, such as the Symphony and Rhapsody branded devices. These are programmable devices with memory and microprocessors comprising circuits for receiving, formatting, and processing electric signals collected by implanted probes bearing cardiac electrodes, and delivering stimulation impulses to these electrodes. It is possible to transmit to the device by telemetry the software, which will be stored and carried out to implement the functions of the invention described below. Adaptation of these apparatuses and creation of suitable software programming to implement the functions of the inventions described herein are deemed to be within the abilities of a person of ordinary skill in the art and a matter of design choice and will not be described in detail herein.

FIG. 1 schematically represents a cardiac muscle with its four cavities: right atrium RA, left atrium LA, right ventricle RV, and left ventricle LV. To allow a bi-ventricular stimulation, probes are implanted for stimulation of each ventricle. Right ventricle RV receives a probe 10 comprising a right ventricular electrode 12. It is a probe of a known type, for example, as disclosed in EP-A-0 950 426, assigned herewith to ELA Médical, to which reference is made and thus will not be described in more detail. Left ventricle LV is stimulated by a probe 20 equipped with a ventricular left electrode 22. The left ventricular cavity not being directly accessible, its stimulation is operated by a probe located in the coronary sinus (like the one described in EP-A-1 374 945 and its counterpart U.S. Patent Application No. 2004/0059401, both assigned herewith to ELA Médical, or by an epicardic probe, whose electrode 22 is placed on an external wall of the myocardium in a site allowing stimulation of the left ventricle.

The electrodes 12 and 22 of probes 10 and 20 are connected to terminals 14 and 24, respectively, of a generator 30, which includes various circuits for analyzing signals and stimulation, and means for processing the signals, these circuits being schematized by block 32.

To allow a satisfactory resynchronization of contraction of the ventricles with fine optimization of the hemodynamic state of the patient, an inter-ventricular delay DIV is applied between the respective moments of stimulation of the left and right ventricles. Indeed, a simultaneous stimulation of the two ventricles is not necessarily optimal, in that it does not lead inevitably to a synchronous contraction of the two ventricles, because the conduction times within the myocardium are not necessarily the same on the right and left sides of the heart and can depend on multiple factors, as well as on the site of the left ventricular probe, according to whether the probe is located in the coronary sinus or is an epicardic probe. It is thus advantageous to establish an inter-ventricular delay between two stimulations, and to adjust this delay so as to resynchronize contraction of the ventricles and to thus lead to a fine optimization of the hemodynamic state.

The introduction of an inter-ventricular stimulation delay and its adjustment can be carried out by suitable programming of the microprocessor of the device so as to start various stimulations at the adapted moments, or by hardware circuits, or by a combination of hardware and software means. The inter-ventricle delay could be: (i) null (0 ms); (ii) positive, the left ventricle being stimulated after the right ventricle with a delay that can reach, for example, 48 ms; or (iii) negative, the right ventricle being stimulated after the left ventricle with a delay that can reach, for example, 48 ms. This inter-ventricular delay is enslaved to a signal directly or indirectly representative of the degree of synchronization of the ventricular contractions. The inter-ventricular delay is adjusted at periodic intervals, according to hemodynamic parameters measured from the exterior (for example, by echography) or continuously by an implanted sensor 34 (e.g., a sensor for determining peak endocardial acceleration PEA, an intracardiac sensor of bio-impedance, etc.) delivering to the microprocessor an indicator of the degree of synchronization of contractions of the right and left ventricles.

These techniques of hemodynamic analysis of the state of the patient and of adjustment of the parameters of operation of an enslaved device in themselves are known and will not be described more in detail. One can refer in particular, in addition to the above-mentioned EP-A-1 108 446 and its counterpart U.S. Pat. No. 6,556,866, to EP-A-1 116 497 and its counterpart U.S. Pat. No. 6,604,002, all assigned herewith to ELA Médical, which disclose the manner of collecting an intracardiac bio-impedance signal and varying the inter-ventricular delay by application of stimulation impulses to the respective right and left ventricles in a direction of improvement of the cardiac flow, and thus of the ejection fraction, which is the hemodynamic parameter of reference, and which are incorporated herein by reference.

In one embodiment of the present invention, generator 30, used for this bi-ventricular stimulation with a variable inter-ventricular delay, is a pacemaker generator of double chamber type originally envisaged for an atrio-ventricular stimulation (a DDD generator). Such a generator 40 includes, among other things, an atrial terminal 50, intended to be connected to a probe equipped with an electrode implanted in right atrium RA, and a ventricular terminal 60, intended to be connected to a probe equipped with an electrode implanted in right ventricle RV. Such a generator 40 must also be able to apply an adjustable atrio-ventricular delay AVD between the moments of stimulation of the atrium and the ventricle. EP-A-1 048 322 and EP-A-1 050 320 and their respective counterparts, U.S. Pat. Nos. 6,397,105 and 6,343,231, all assigned herewith to ELA Médical, describe such DDD generators, which include means for reprogramming, if necessary, the atrio-ventricular delay, automatically.

To operate a bi-ventricular stimulation instead of an atrio-ventricular stimulation, it is sufficient to connect to this DDD generator 40 a right ventricular stimulation probe 10 and a left ventricular stimulation probe 20 respectively at terminals 50 and 60, and to modify the atrio-ventricular delay control software AVD so as to adjust this delay with the desired value of the inter-ventricular delay DIV. If generator DDD 40 makes it possible, technically, to program the ventricular delay control software AVD with an indifferently negative, null, or positive value (although, physiologically, stimulation of the atrium must always precede that of the ventricle), the circuit of the impulse generator could be directly used for bi-ventricular stimulation, by controlling in the way indicated above the information representative of the hemodynamic state of the patient. If generator 40 does not make it possible to program negative atrio-ventricular time, it will then be necessary to add to the generator 30 bi-ventricular stimulation programmable switching means 36 able to permute electrically the two terminals 14 and 24 to be able indifferently to stimulate one ventricle earlier or later in comparison with the other, according to the position of this switch 36.

One skilled in the art will appreciate that the present invention can be practiced by other than the described embodiments, which are presented for purposes of illustration and not of limitation.

I claim:

1. An active implantable medical device of the dual chamber pacemaker type comprising:
    a generator of a dual chamber pacemaker type;
    an atrial terminal and a ventricular terminal;
    atrial and ventricular stimulation circuits respectively delivering pacing pulses at the atrial and ventricular terminals;
    an adjustable atrio-ventricular delay between delivery of consecutive pacing pulses at the atrial and ventricular terminals; and
    means for establishing an adjustable inter-ventricular delay between moments of application of pacing pulses deliverable to a right ventricle and a left ventricle during the same cardiac cycle, wherein said atrio-ventricular delay is adjusted with the value of said inter-ventricular delay, and the atrial stimulation circuit and the atrial terminal are adapted for delivery of pacing pulse to one of the left ventricle and the right ventricle, and the ventricular stimulation circuit and the ventricular terminal are adapted for delivery of pacing pulse to the other of the left ventricle and the right ventricle.

2. The device of claim 1, wherein the adjusted atrio-ventricular delay is selected to be one of positive, null, and negative values.

3. The device of claim 1, in which the adjusted atrio-ventricular delay is selected to be one of a positive and a null value, and further comprising a programmable switch coupled to the atrial and ventricular terminals having a first condition in which the atrial stimulation circuit delivers a pacing pulse to the atrial terminal before the ventricular stimulation circuit delivers a pacing pulse to the ventricular terminal during the same cardiac cycle, and a second condition in which the atrial stimulation circuit delivers a stimulation pulse to the atrial terminal after the ventricular stimulation circuit delivers a stimulation pulse to the ventricular terminal during the same cardiac cycle.

4. The device of claim 1, further comprising:
    a sensor having an output representative of a hemodynamic parameter; and
    control means for varying the adjustable atrio-ventricular delay in a direction of the improvement of the hemodynamic parameter according to a signal delivered by said sensor.

5. The device of claim 1, further comprising:
    means for analyzing a parameter representative of a degree of desynchronization between ventricles over a cardiac cycle and having an output signal corresponding to the degree of synchronization; and
    control means for varying the adjustable atrio-ventricular delay in a direction of the reduction of the degree of desynchronization in response to said output signal delivered by the means of analysis.

6. A method of bi-ventricular stimulation using a generator of a dual chamber pacemaker type having an atrial terminal and a ventricular terminal, atrial and ventricular stimulation circuits for delivering pacing pulses at the atrial and ventricular terminals, and an adjustable atrio-ventricular delay between moments of application of the pacing pulses respectively delivered at the atrial and ventricular terminals, comprising:
    establishing an adjustable inter-ventricular delay between moments of application of the pacing pulses delivered to the right and left ventricular electrodes during the same cardiac cycle;
    adapting the atrial stimulation circuit to deliver a pacing pulse at the atrial terminal suitable for a ventricular stimulation;
    providing said atrio-ventricular delay with the value of said inter-ventricular delay and applying a bi-ventricular stimulation using said atrial and ventricular stimulation circuits and said inter-ventricular delay.

7. The method of claim 6, further comprising adjusting said interventricular delay to have one of a positive, null, and negative value.

8. The method of claim 6, further comprising:
    selecting the adjusted atrio-ventricular delay from one of a positive and a null value; and
    controlling whether the atrial stimulation circuit delivers a pacing pulse to the atrial terminal before or after the ventricular stimulation circuit delivers a pacing pulse to the ventricular terminal during the same cardiac cycle so as to employ a positive atrio-ventricular delay.

9. The method of claim 6, further comprising monitoring a hemodynamic parameter and varying the adjustable atrio-ventricular delay in a direction of the improvement of the monitored hemodynamic parameter.

10. The method of claim 6, further comprising:
    analyzing a parameter representative of a degree of desynchronization between ventricles over a cardiac cycle;
    generating an output signal corresponding to the degree of desynchronization; and
    varying the adjustable atrio-ventricular delay in a direction of the reduction of the degree of desynchronization in response to the generated output signal.

11. An active implantable medical device comprising:
a first lead, comprising a first electrode, of the right ventricular type,
a second lead, comprising a second electrode, of the left ventricular type,
a dual-chamber pacing pulse generator, comprising:
- a first output terminal, linked to the right ventricular electrode,
- a second output terminal, linked to the left ventricular electrode, means for right and left pacing by delivering on said first and second output terminals, respective pacing pulses, and means for establishing an adjustable delay between the moments of application of the pulses respectively delivered at the first and second output terminals, allowing the device to operate in a mode of resynchronization of the ventricular contractions for the treatment of heart failure, the value of said delay being then adjusted to a value of interventricular delay (IVD), wherein said means for establishing an adjustable delay further comprises means for adjusting said delay to a duration not higher than 48 ms in absolute value.

12. A method of use for a dual chamber pacemaker comprising:
a first output terminal,
a second output terminal,
means for delivering pacing pulses to the first and second output terminals, respectively, and
means for establishing an adjustable delay between a moment of delivery of the pacing pulses respectively delivered at the first and second output terminals, wherein the means for establishing an adjustable delay comprises adjusting said delay to a duration not higher than 48 ms in absolute value, in combination with
- a first lead comprising a right ventricular electrode linked to the first output terminal, and
- a second lead comprising a left ventricular electrode linked to the second output terminal, for obtaining an active implantable medical device comprising a mode of resynchronization of the ventricular contractions intended to the treatment of heart failure, and adjusting the value of said adjustable delay to a value of interventricular delay (IVD).

* * * * *